(12) United States Patent
Greep et al.

(10) Patent No.: US 11,141,577 B2
(45) Date of Patent: Oct. 12, 2021

(54) FLUID SYSTEM CONNECTOR

(71) Applicant: Megadyne Medical Products, Inc., Draper, UT (US)

(72) Inventors: Darcy W. Greep, Herriman, UT (US); Chad S. Frampton, American Fork, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 0 days.

(21) Appl. No.: 16/583,791

(22) Filed: Sep. 26, 2019

(65) Prior Publication Data

US 2020/0094035 A1    Mar. 26, 2020

Related U.S. Application Data

(63) Continuation-in-part of application No. 16/141,634, filed on Sep. 25, 2018.

(51) Int. Cl.
| | | |
|---|---|---|
| *A61M 39/10* | (2006.01) | |
| *A61B 18/00* | (2006.01) | |
| *A61B 90/00* | (2016.01) | |

(52) U.S. Cl.
CPC ......... *A61M 39/1011* (2013.01); *A61B 18/00* (2013.01); *A61B 90/08* (2016.02); *A61M 39/1055* (2013.01); *A61B 2218/008* (2013.01); *A61M 2205/02* (2013.01)

(58) Field of Classification Search
CPC ......... F16L 21/04; F16L 17/025; F16L 17/03; F16L 27/08; F16L 27/0816; F16L 27/082; F16J 15/025; A61M 39/1011; A61M 39/1055

USPC ................ 285/110, 111, 112, 215, 275, 910; 277/607, 615

See application file for complete search history.

(56) References Cited

U.S. PATENT DOCUMENTS

| | | | | |
|---|---|---|---|---|
| 2,271,777 | A | * | 2/1942 | Nathan ................ F16L 17/025 277/615 |
| 3,666,297 | A | | 5/1972 | Marks |
| 3,702,193 | A | | 11/1972 | Flegel |

(Continued)

FOREIGN PATENT DOCUMENTS

EP          1069362 A2 *  1/2001  .......... F16L 27/0828

OTHER PUBLICATIONS

U.S. Appl. No. 16/141,634, filed Sep. 25, 2018, Greep et al.

(Continued)

*Primary Examiner* — Zachary T Dragicevich
(74) *Attorney, Agent, or Firm* — Workman Nydegger

(57) ABSTRACT

A universal fluid system connector creates an airtight seal between a variety of smoke evacuation system receptacles and various hoses. The universal connector includes a body, a seal having a plurality of radially extending flexible fins, and a swivel. A plurality of fins on the seal are disposed along the length of the body with the outer edges of the fins forming a frustoconical shape. The fins also include one or more flexion zones of various stiffness and one or more flexible fin extensions. The fins deform against the inner wall of a receptacle and form an airtight friction fit between the universal connector and the receptacle, regardless of the taper angle, size, threads, or other features of the receptacle. The swivel facilitates rotational movement between the universal fluid system connector and an associated hose.

20 Claims, 10 Drawing Sheets

(56) References Cited

U.S. PATENT DOCUMENTS

| | | |
|---|---|---|
| 3,767,233 A | 10/1973 | Hodge |
| D246,855 S | 1/1978 | Treloar |
| D254,505 S | 3/1980 | Parsons et al. |
| 4,194,750 A | 3/1980 | Sovish |
| 4,346,922 A | 8/1982 | Ohtsuga |
| 4,625,998 A * | 12/1986 | Draudt .......... 285/110 |
| 4,646,204 A | 2/1987 | Brauer |
| 4,946,204 A * | 8/1990 | Boticki |
| D333,178 S | 2/1993 | Novy |
| D347,467 S | 5/1994 | Medvick |
| 5,653,452 A * | 8/1997 | Jarvenkyla ......... 277/607 |
| D439,636 S | 3/2001 | Hamilton |
| 6,494,463 B1 | 12/2002 | Rank |
| D612,939 S | 3/2010 | Boone, III et al. |
| 7,677,610 B2 * | 3/2010 | Schwarz |
| D639,657 S | 6/2011 | Hoyt et al. |
| 8,262,094 B2 | 9/2012 | Beele |
| D677,766 S | 3/2013 | Chen |
| D712,014 S | 8/2014 | Guest |
| D726,287 S | 4/2015 | Steele |
| D733,842 S | 7/2015 | Allred et al. |
| D735,853 S | 8/2015 | Pa |
| D736,914 S | 8/2015 | Schultz |
| D745,116 S | 12/2015 | Lehmann |
| D770,598 S | 11/2016 | Steele |
| D817,446 S | 5/2018 | Kinzel et al. |
| D826,046 S | 8/2018 | Niles |
| D835,267 S | 12/2018 | Gilbert et al. |
| 2002/0147429 A1 | 10/2002 | Cowan et al. |
| 2007/0001448 A1 | 1/2007 | Navarro |
| 2020/0096142 A1 | 3/2020 | Greep et al. |

OTHER PUBLICATIONS

U.S. Appl. No. 29/664,475, filed Sep. 25, 2018, Greep et al.
Non-Final Office Action for U.S. Appl. No. 29/664,475 dated Nov. 18, 2019.
Non-Final Office Action for U.S. Appl. No. 29/664,475 dated Apr. 24, 2020.
Notice of Allowance for U.S. Appl. No. 29/664,475 dated Aug. 3, 2020.
Non-Final Office Action for U.S. Appl. No. 16/141,634 dated Sep. 22, 2020.
Non-Final Rejection dated Sep. 22, 2020 for U.S. Appl. No. 16/141,634.
Notice of Allowance received for U.S. Appl. No. 16/141,634, dated Jan. 26, 2021, 5 pages.

* cited by examiner

FLUID SYSTEM CONNECTOR

CROSS-REFERENCE TO RELATED APPLICATION

This application is a continuation-in-part application of U.S. patent application Ser. No. 16/141,634, filed Sep. 25, 2018, and entitled Fluid System Connector, the entire content of which is incorporated herein by reference.

BACKGROUND

Technical Field

The present disclosure relates to fluid systems, such as smoke evacuation systems used in electrosurgical systems. More specifically, the present disclosure relates to devices for connecting hoses to fluid evacuation devices.

The Relevant Technology

As is known to those skilled in the art, modern surgical techniques typically employ radio frequency (RF) power to cut tissue and coagulate bleeding encountered in performing surgical procedures. This type of surgery is known as electrosurgery. Electrosurgery is widely used and offers many advantages, including the use of a single surgical instrument for both cutting and coagulating tissue. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue through cauterization. The return electrode carries the same RF signal provided to the electrode or tip of the electrosurgical instrument, after it passes through the patient, thus providing a path back to the electrosurgical generator.

Electrosurgical instruments communicate electrical energy to a target tissue of a patient to cut the tissue and/or cauterize blood vessels within and/or near the target tissue. This cutting/cauterization results in smoke released into the air that can be unpleasant and obstructive to the view of a practitioner. Many electrosurgical systems may therefore employ an evacuation system that captures the resulting smoke and directs it through a filter and exhaust port, away from practitioners and/or patients.

A smoke evacuation system typically includes a hand piece or wand having one end of a hose connected thereto. A second end of the hose can be connected to an evacuation device that creates suction to draw the smoke into the hand piece or wand and through the hose. A common issue faced with typical smoke evacuation systems is connecting the hose to the smoke evacuation device in a secure and airtight manner. The hoses on typical hand pieces or wands can come with any number of different connectors for connecting to smoke evacuation devices. Likewise, typical smoke evacuation devices can come with any number of different receptacles or connection features to which the hose is to be connected. Too often the hose connectors and the smoke evacuation device receptacles/connection features are incompatible or do not connect together in a secure and airtight manner. As a result, reduced suction may be experienced at the hand piece or wand and smoke may undesirably escape at the faulty connection between the hose and the smoke evacuation device.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates to fluid systems, such as smoke evacuation systems used in electrosurgical systems. More specifically, the present disclosure relates to devices for connecting hoses to fluid evacuation devices. Hose connectors are generally designed to be compatible with only one or a limited number of fluid evacuation device receptacles due to the unique geometry or other features of the receptacle. The fluid system connectors of the present disclosure enable universal compatibility between the connector and any number of evacuation device receptacles.

In an embodiment of the present disclosure, a universal fluid system connector assembly includes a body having a proximally extending stem, a seal disposed about at least a portion of the body, and a swivel. The seal has a plurality of flexible fins disposed along the length of the body, each fin having a diameter. The swivel is connectable to the stem of the body and is configured to connect to a vacuum hose and enable relative rotation between the body and the hose.

In an embodiment of the present disclosure, a universal fluid system connector assembly includes a body, a seal disposed about at least a portion of the body, and a swivel. The body has a length extending between a distal end thereof and a proximal end thereof, a fluid passageway extending through the length of the body, a proximally extending stem, and a plurality of ribs disposed along at least a portion of the length of the body, each rib extending at least partially around the body and extending radially outward from the body. The seal has a plurality of flexible fins disposed along the length of the body, each fin having a diameter. In such an embodiment, the diameters of the fins may increase from a distal end of the connector to the proximal end of the connector so that the plurality of fins form a frustoconical shape. Also, the seal may include a plurality of recessed portions disposed around an inner surface of the seal. The body may include a plurality of ribs that correspond in position to the recessed portions of the seal when the seal and body are joined together. In this embodiment, the ribs of the body engage the recessed portions of the seal to retain the seal around the body. The swivel is connectable to the stem and is configured to facilitate relative rotational movement between the body and a vacuum hose connected to the swivel.

In an embodiment of the present disclosure, a universal fluid system connector assembly includes a body, a seal, and a swivel. The body has a length extending between a distal end thereof and a proximal end thereof and a proximally extending stem. The seal is disposed about at least a portion of the body. The seal includes a plurality of flexible fins having outer edges that form a frustoconical shape, which tapers down toward the distal end of the connector. This embodiment may also include an outer frustoconical shell at least partially surrounding the outer edges of the fins. The fins may be curved so that the plurality of fins spirals radially around the body. The swivel is connectable to the stem and is configured to facilitate relative rotational movement between the body and a vacuum hose connected to the swivel.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Additional features and advantages of the disclosed embodiments will be set forth in the description which follows, and in part will be obvious from the description, or may be learned by the practice of the disclosure. These and other features will become more fully apparent from the following description and appended claims or may be learned by the practice of the present disclosure.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Figure 1:
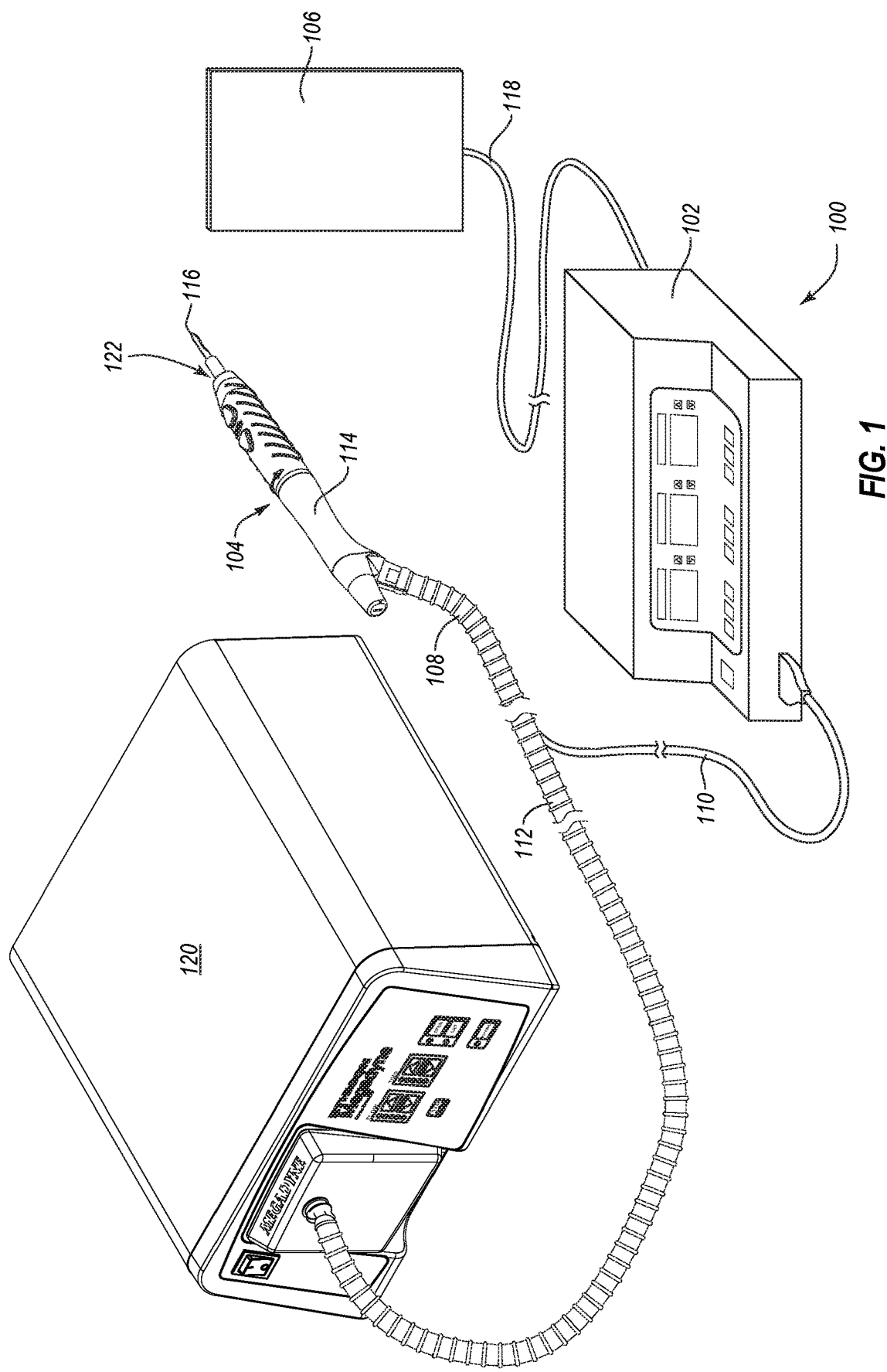
FIG. 1 illustrates an exemplary electrosurgical system.

The present disclosure relates to smoke evacuation devices associated with electrosurgical instruments and other hand-held instruments that produce smoke or cause smoke to be produced during use. FIG. 1, for example, illustrates an exemplary electrosurgical system 100. The illustrated embodiment includes a signal generator 102, an electrosurgical instrument 104, and a return electrode 106. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates electrical energy from generator 102 to electrosurgical instrument 104. The illustrated utility conduit 108 also includes a vacuum hose 112 that conveys captured/collected smoke and/or fluid away from a surgical site and to, for example, a smoke evacuation device 120. In some embodiments, the vacuum hose 112 can also be used to deliver fluids or gases to a surgical site. Additionally, in some embodiments, such as that illustrated in FIG. 1, cable 110 can extend through at least a portion of vacuum hose 112 and to electrosurgical instrument 104.

Generally, electrosurgical instrument 104 includes a hand piece or pencil 114, an electrode tip 116, and an inlet or nozzle 122. Electrosurgical instrument 104 communicates electrical energy to a target tissue of a patient to cut the tissue and/or cauterize blood vessels within and/or near the target tissue. Specifically, an electrical discharge is delivered from electrode tip 116 to the patient in order to cause heating of cellular matter of the patient that is in close contact with electrode tip 116. The heating takes place at an appropriately high temperature to allow electrosurgical instrument 104 to be used to perform electrosurgery. Smoke created during the electrosurgical procedure is drawn into the electrosurgical instrument 104 through the nozzle 122 and conveyed to smoke evacuation device 120 through the vacuum hose 112. Return electrode 106 is connected to generator 102 by a cable 118 in order to complete the circuit and provide a return electrical path to wave generator 102 for energy that passes into the patient's body.

In practice, the various components of a system, such as electrosurgical system 100, are commonly acquired separately from one another and later assembled into a complete system. For instance, a hospital or other surgical practice may acquire a generator 102 and/or a smoke evacuation device 120 as the centerpieces of such a system because these components may be the most expensive and/or have the longest lifespan of the system components. On the other hand, the hospital or surgical practice may acquire electrosurgical instruments (e.g., instrument 104 (including the associated utility conduit 108)) and return electrodes (e.g., electrodes 106) on a regular or periodic basis due to their disposable nature or the shorter lifespans of these components.

Because of the wide range of electrosurgical instruments and return electrodes that are available from a variety of providers, a hospital or surgical practice may want to change what electrosurgical instrument and/or return electrode it uses. As can be expected, some challenges can arise when switching to a new electrosurgical instrument and/or return electrode. For instance, if a hospital or surgical practice wants to switch to a new electrosurgical instrument, compatibility of the new electrosurgical instrument with the existing system components (e.g., generator 102 and/or a smoke evacuation device 120) needs to be confirmed.

One area of compatibility that needs to be considered, but is too often overlooked, is whether the connection features of a vacuum hose and the smoke evacuation device enable the vacuum hose to be connected to the smoke evacuation device in a secure and airtight manner. In some cases, the connection features of the vacuum hose and the smoke evacuation device may be threads that do not properly mate to create a secure connection. In other cases, the connection features may be friction fit features (e.g., tapers) that do not sufficiently correspond to one another (e.g., in angle, size, length, etc.) to create a secure connection. In still other cases, the connection features may be entirely different from one another (e.g., one component has threads and the other component has a friction fit taper).

A poor connection between the vacuum hose 112 and the smoke evacuation device 120 can lead to smoke or other fluids leaking from the connection. As a result of such incompatibilities (e.g., between the connection features of the smoke evacuation device 120 and the vacuum hose 112), hospitals and surgical practices often have little choice but to continue using the same electrosurgical instruments, even if a change to a new electrosurgical instrument is desired.

As explained in greater detail below, embodiments of the present disclosure relate to universal connectors that enable secure and airtight connections between substantially any combination of electrosurgical instruments and smoke evacuation devices. As a result, an electrosurgical instrument fitted with a universal connector as disclosed herein can be safely and effectively used with substantially any available smoke evacuation device. Additionally, substantially any available electrosurgical instrument can be fitted or retrofitted with the universal connectors disclosed herein so that the electrosurgical instrument can be safely and effectively used with substantially any available smoke evacuation device.

Before proceeding further, it is noted that reference is made herein to the evacuation of smoke and components that facilitate such function. It will be appreciated that references to "smoke" is merely for simplicity and convenience and is not intended to limit the disclosed and claimed embodiments to evacuation of only smoke. Rather, the disclosed and claimed embodiments may be used to evacuate substantially any type of fluid, including liquids, gases, vapors, smoke, or combinations thereof. Additionally, rather than simply evacuating fluid, it is contemplated that at least some of the embodiments may be used to deliver fluids to a desired location, such as a surgical site. As used herein, the term "fluid" includes gases, bulk liquids, and/or liquid vapor, which can include liquids—biologic in origin or otherwise—obtained from or introduced into a surgical site (e.g., water, saline, lymph, blood, exudate, pyogenic discharge, and/or other fluid).

Additionally, reference is made herein to electrosurgical instruments that have vacuum hoses associated therewith to which the disclosed universal connectors may be connected. It will be appreciated that the disclosed universal connectors can be connected to vacuum hoses that are associated with hand pieces or other implements other than electrosurgical instruments. For instance, vacuum hoses and the disclosed universal connectors can be used in connection with dental instruments (e.g., drills, polishing tools, scalers, compressed air tools, suction tools, irrigation tools, carries detection tools, water flossing tool (e.g., waterpik)), soldering tools (e.g., heated tools, smoke collection tools, de-soldering tools), high speed grinding and polishing tools (e.g., Dremel tools, carving tools, manicure tools, dental lab grinders/polishers), laser treatment instruments, laser surgical instruments, light probes, suction handles (e.g., Yankauer), blasting tools (e.g., sandblast, gritblast), shockwave therapy tools, ultrasonic therapy tools, ultrasonic probe tools, ultrasonic surgical tools, adhesive application instruments, glue guns, pneumatic pipettes, welding tools, RF wrinkle therapy hand pieces, phaco hand pieces, shears, shaver, or razor hand pieces, micro drill hand pieces, vacuum hand pieces, small parts handling hand pieces, tattoo needle handles, small torch hand pieces, electrology hand pieces, low speed grinding, polishing and carving tools, permanent makeup hand pieces, electrical probe hand pieces, ferromagnetic surgical hand pieces, surgical plasma hand pieces, argon beam surgical hand pieces, surgical laser hand pieces, surgical suction instruments (e.g., liposuction cannulas), surgical suction cannulas, microdermabrasion hand pieces, fiberoptic camera handles, microcamera hand pieces, pH probe hand pieces, fiberoptic and LED light source hand pieces, hydrosurgery hand pieces, orthopedic shaver, cutter, burr hand pieces, wood burning tools, electric screwdrivers, electronic pad styluses, and the like.

Figure 2:
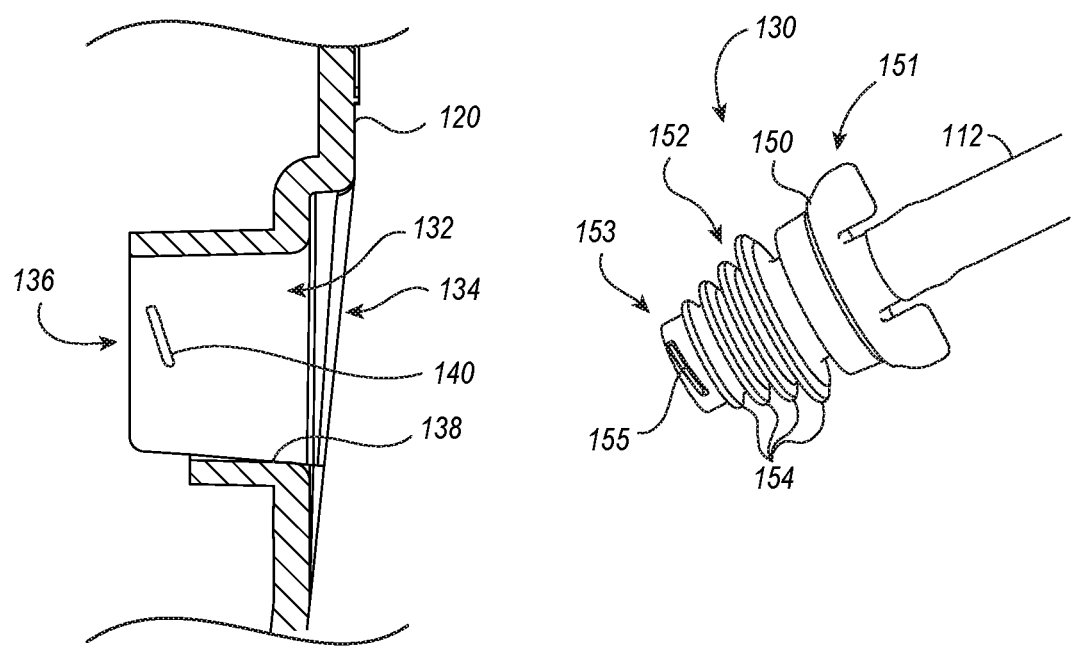
FIG. 2 illustrates a side view of an exemplary universal fluid system connector along with a cross-sectional view of a fluid evacuation device receptacle.

Attention is now directed to FIG. 2, which illustrates a partial cross-sectional view of the smoke evacuation device 120 and a universal connector 130 that can be selectively connected thereto. More specifically, FIG. 2 illustrates a cross-sectional view of an inlet or receptacle 132 of the smoke evacuation device 120. Additionally, the universal connector 130 is connected to a vacuum hose 112 that may be associated with electrosurgical instrument 104 or another hand piece or instrument.

The receptacle 132 illustrated in FIG. 2 includes features commonly found in receptacles of available smoke evacuation devices. For instance, the receptacle 132 includes an exterior opening 134 and an interior opening 136. The exterior opening 134 is configured to enable a vacuum hose connector to be inserted into the receptacle 132. The interior opening 136 enables fluid communication between the smoke evacuation device 120 and the vacuum hose 112 so that smoke in the vacuum hose 112 can be drawn into the smoke evacuation device 120.

The illustrated receptacle 132 also includes a tapered wall 138 extending between the openings 134, 136 and a thread 140 formed on the tapered wall 138. The tapered wall 138 and the thread 140 are common connection features that are intended to secure a vacuum hose connector within the receptacle 132. For instance, the tapered wall 138 may have a taper that corresponds to a taper of a vacuum hose connector so that a friction fit is created when the vacuum hose connector is inserted into the receptacle 132. Similarly, the thread 140 may mate with a corresponding thread on a vacuum hose connector. As noted elsewhere herein, however, the connection features in the receptacle 132 may be designed for use with a specific vacuum hose connector and may not be suited for all vacuum hose connectors. As a result, the use of different vacuum hose connectors may not result in a secure and airtight seal between the receptacle 132 and the vacuum hose connector.

The universal connector 130 shown in FIG. 2 is designed to be used with a variety of smoke evacuation devices regardless of the specific configurations of the receptacles or connection features thereof. More specifically, the universal connector 130 is configured to be securely received within a variety of receptacles and create airtight seals therewith.

The illustrated universal connector 130 includes a body 150 having a proximal end 151 and a distal end 153 and a seal 152 disposed on or about a portion of the length of the body 150. The seal 152 includes a plurality of fins 154 along the length of the body 150, with each fin 154 extending circumferentially around the body 150. As will be described in greater detail below, at least portions of the fins 154 can be flexible so that the fins can conform to the tapered wall 138 of the receptacle 132 so as to create a secure and airtight connection between the universal connector 130 and the receptacle 132.

Together the fins 154 have a generally conical or frustoconical shape. In other words, the fins 154 have diameters that increase along the length of the body 150 so that the outer edges of the fins form a frustoconical shape. Specifically, the fin 154 adjacent the distal end 153 of the universal connector 130 has a first diameter, the next most distal fin 154 has a second diameter that is larger than the first diameter, the third most distal fin 154 has a third diameter that is larger than the second diameter, and the most proximal fin 154 has a fourth diameter that is larger than the third diameter.

In the illustrated embodiment, the difference between the first diameter and the second diameter is about the same as the difference between the second diameter and the third diameter. In other words, the three most distal fins 154 have a profile with a generally consistent taper. However, the difference between the third diameter and the fourth diameter is larger than the differences between the first, second, and third diameters. As a result, the profile taper of the plurality of fins 154 steepens near the proximal end of the universal connector 130.

While the seal 152 is illustrated with four fins 154, it will be appreciated that the seal 152 may include fewer or more than four fins 154. Similarly, the diameters of the fins 154 may vary from one embodiment to another. For instance, some fins may have similar or identical diameters to each other. In some embodiments, the differences between diameters of adjacent fins may all be the same as or different from one another, or combinations thereof.

The body 150 of the universal connector 130 may optionally include a thread 155. The thread 155 may be disposed near the distal end 153 of the universal connector 130 and be configured to engage the thread 140 in the receptacle 132.

Figure 3:
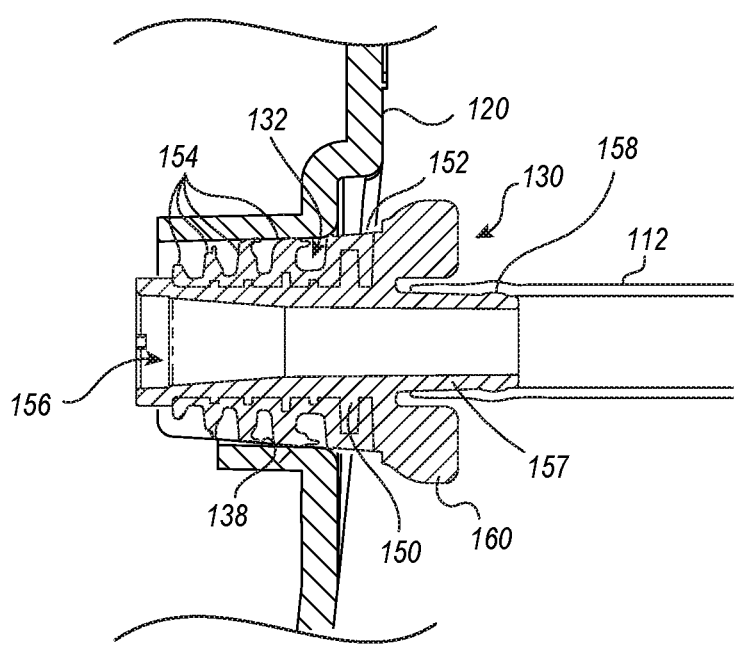
FIG. 3 illustrates a cross-sectional side view of an exemplary universal fluid system connector inserted into a fluid evacuation device receptacle.

With continuing attention to FIG. 2, attention is now also directed to FIG. 3. FIG. 3 illustrates the universal connector 130 inserted into the receptacle 132 in order to connect the vacuum hose 112 to the smoke evacuation device 120. As can be seen, the outer tips of fins 154 engage the tapered wall 138 and flex rearward (e.g., towards the proximal end of the universal connector 130) when the universal connector 130 is inserted into the receptacle 132. The engagement of the fins 154 and the tapered wall 138 creates an airtight seal therebetween. As a result, smoke conveyed from the vacuum hose 112 to the smoke evacuation device 120 cannot escape between the tapered wall 138 and the fins 154. Additionally, the friction between the fins 154 and the tapered wall 138 can securely hold the universal connector 130 in the receptacle 132.

One will appreciate that the degree to which the fins 154 bend in response to inserting the universal connector 130 depends on the relative dimensions of the fins 154 and receptacle 132 as well as the magnitude of the force being applied on the universal connector 132. As can be seen in FIG. 3, some fins 154, such as the larger fins toward the proximal end 151 of the universal connector 130 flex to a greater degree than more distal fins 154. In some cases, one or more fins 154 may not flex at all, such as the distal most fin 154 illustrated in FIG. 3.

In this way, the universal connector 130 may be compatible with receptacles 132 of various sizes, tapers, and shapes because at least one or more fins 154 of various diameters and sizes will engage the tapered wall 138 of the receptacle 132. One will also appreciate that the universal connector 130 may form an airtight seal within a receptacle 132 having threaded features because one or more fins 154 may flex and/or conform to the internal threaded surface of the tapered wall 138.

Figure 4:
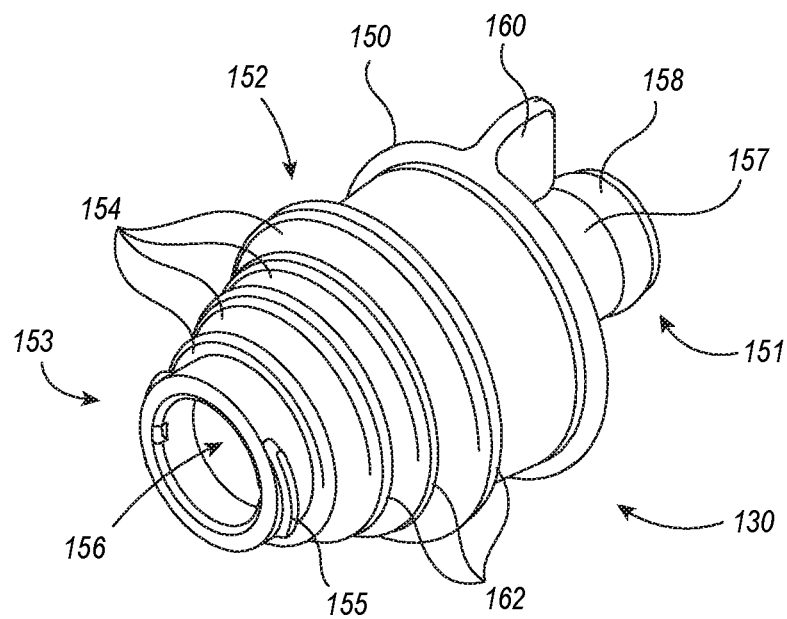
FIG. 4 illustrates a perspective view of an exemplary universal fluid system connector.

In order to illustrate the universal connector 130 in more detail, FIG. 4 shows a perspective view of an exemplary universal connector 130 in isolation. The illustrated universal connector 130 includes a seal 152 having a plurality of ribs 154 extending at least partially around a body 150, which are disposed along the length of the body 150 and varied in diameter to form a frustoconical shape. In addition, a fluid passageway 156 extends through an interior space of the body 150 from the distal end 153 to the proximal end 151. The body 150 also includes threaded features 155 near the distal end 153, similar to those noted above with reference to FIGS. 2 and 3.

Furthermore, the proximal end 151 includes a stem 157. The fluid passageway 156 extends through an open at an open proximal end of the stem 157 (as can be seen in FIG. 3). In some embodiments, the outer surface of the stem 157 may be tapered such that an outer dimension of the stem 157 decreases closer to the proximal end of the stem 157. In other embodiments, the stem 157 may have a generally constant outer dimension along the length thereof. In yet other embodiments, the stem 157 may have an outer dimension that increases closer to the proximal end of the stem 157.

In the illustrated embodiment, a hose retaining lip 158 is disposed around an outer surface of the stem 157. At least a portion of the stem 157, including the hose retaining lip 158, can be inserted into the end of a hose, such as the vacuum hose 112 described herein, such that the hose can extend over the retaining lip 158 to form an airtight fit between the fluid passageway 156 and the vacuum hose 112. The vacuum hose 112 can be secured to the body 150 of the universal connector 130 via friction between the vacuum hose 112 and the retaining lip 158.

Figure 5A:
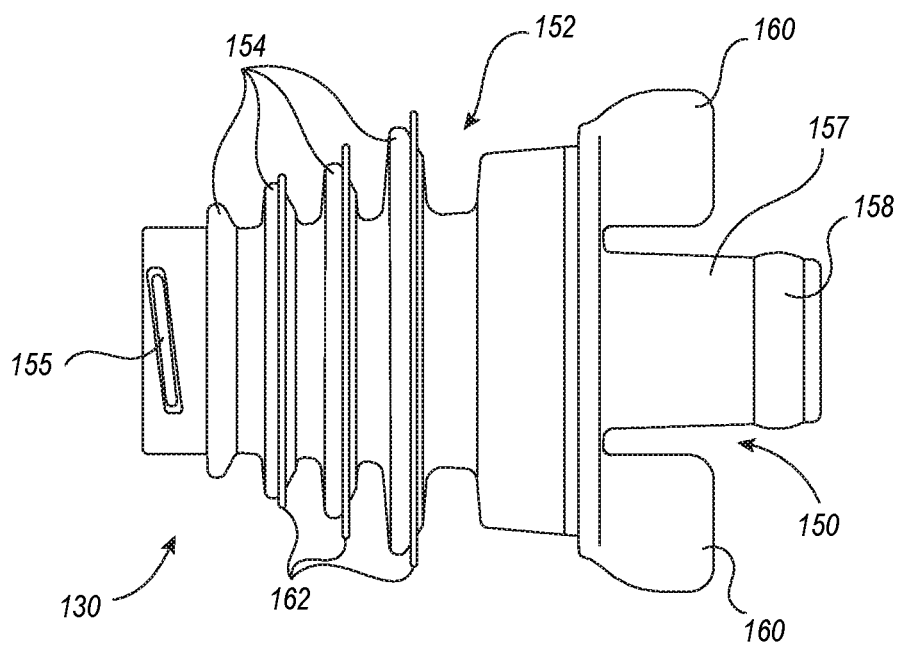
FIG. 5A illustrates a side view of an exemplary universal fluid system connector.
Figure 5B:
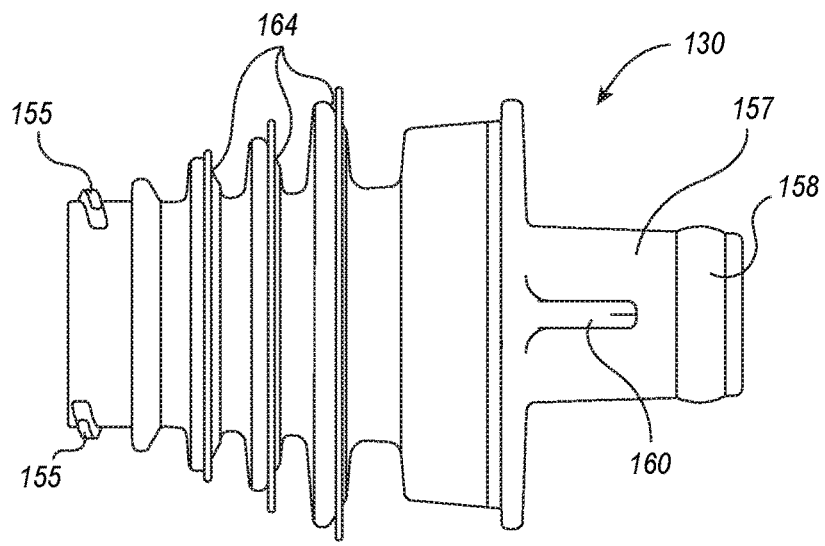
FIG. 5B illustrates another side view of an exemplary universal fluid system connector.

In addition, the body 150 may include one or more tabs 160 extending proximally therefrom to aid a user in gripping and pushing/twisting the universal connector 130 into a receptacle or pulling/twisting the universal connector 130 out of a receptacle. The tabs 160 illustrated in FIGS. 2-5B, 7A, 7C-9, and 10 are integrally formed with the body 150 but may also be formed separately from the body 150 and rigidly connected thereto. Also, in one or more other embodiments of a universal connector 130, the number, shape, size, and configuration of the tabs may vary. For example, in the embodiment shown in FIG. 5A, the body 150 includes two generally rectangular tabs 160. In another embodiment, the body 150 may comprise one tab 160 or more than two tabs 160 tabs that may be circular, triangular, or any other shape. The tabs 160 may assist a user in gripping the universal connector 130 when inserting the universal connector 130 into a receptacle or withdrawing the universal connector 130 from a receptacle. In cases where the receptacle includes a threaded feature, the tabs 160 may allow the user to more easily twist the universal connector 130 onto or off of the threads 140 as needed. For reference, FIG. 5B illustrates a side view of the universal connector 130 rotated 90-degrees to showing the tabs 160 and threads 155 rotated accordingly.

Referring back to FIG. 5A, the seal 152 of the universal connector 130 may also include fin extensions 162 disposed around one or more of the fins 154. As illustrated in FIG. 5A, the fin extensions 162 may comprise material disposed at or near the outer edge of the fin 154 and extending radially outward beyond the outer edge of the fins 154. The fin extensions 162 may be thinner than the fins 154 so that they are less stiff than the fins 154. Referring briefly back to FIG. 4, one can see that the fin extensions 162 extend circumferentially around each fin 154 on which they are disposed. In one embodiment, the fin extensions 154 may extend only partially around the fins 154. In another embodiment, each fin may have more or less than one fin extension 162 extending therefrom, including fin extensions 162 that extend completely around the fin 154 and/or only partially around as described. In addition, one or more embodiments may include fin extensions 162 on only one fin 154, on all fins 154, on no fins 154, or on only some fins 154 of the seal 152.

The fin extensions 162 may be added to the proximal edge of one or more of the flexible fins 154 to improve the fit of the universal connector 130 in varying receptacle 132 sizes. The advantage provided by the fin extensions 162 depends on the diameter, thickness, and location on the fin extensions 162 on the fins 154. For example, in an embodiment where the fin extensions 162 on the proximal face of the fins 154, the fin extensions 162 may make virtually no change in the insertion force required to push the universal connector 130 into the receptacle 132. However, in this configuration, the retention and extraction forces may be significantly increased, providing improved functionality of the universal connector 130 and a better fit across a wider range of receptacle 132 sizes and configurations.

The location of the thinner fin extensions 162 on the proximal face of the larger, thicker fins 154 also prevents additional interference upon insertion as the fin extensions 162 are pushed back and away from the fin 154. Once inserted, however, retention and extraction forces may be significantly increased when the fin extension 162 is forced to fold back on itself in order to pull the universal connector 130 out of the receptacle. This folding action increases the overall interference between the fins 154 of the universal connector 130 and the receptacle 132, which increases the retention and extraction forces during use. Also, as noted above, one or more embodiments of the universal connector 130 may include more than one fin extension 162 on each fin 154, and the diameter, thickness and location of the fin extension(s) 162 may be adjusted to alter the required insertion, retention, and extraction forces for improved fit and functionality of the universal connector 130.

In addition to the fin extensions 162 described herein, one or more of the fins 154 may also include a taper 164 at or near the outer edge of the fin 154. FIG. 5B illustrates fins 154 having a taper 164 disposed on a proximal face of each fin 154. The taper 164 may extend partially down the proximal face of the fin 154. In one embodiment, the taper 164 may extend all the way down the face of the fin 154 and/or be angled at varying degrees. Also, in one or more other embodiments, one or all of the fins 154 may have a taper 164 on the distal face of each fin 154. In yet another embodiment, one or more of the fins 154 may have a taper 164 on both faces of the fin 154. One will appreciate, that the various tapers 164 and configurations described herein may be combined in one or more other embodiments to form a variety of fins 154 having a combination of tapers 164 and configurations.

The various tapers 164, fin extensions 164, and other features of the fins 154 described herein may affect the way in which the fins 154 deflect, bend, or otherwise conform to the tapered wall 138 of a receptacle 132, as shown in FIG. 3 and described above. That is, the material thickness of each fin 154 resulting from the angle and/or size of each taper 64 as well as the thickness, number, and size of each fin extension 162, may affect the stiffness of each fin 154. In addition, these features may result in each fin 154 having one or more flexion zones 166, with each flexion zone having a different stiffness than an adjacent flexion zone 166.

Figure 6:
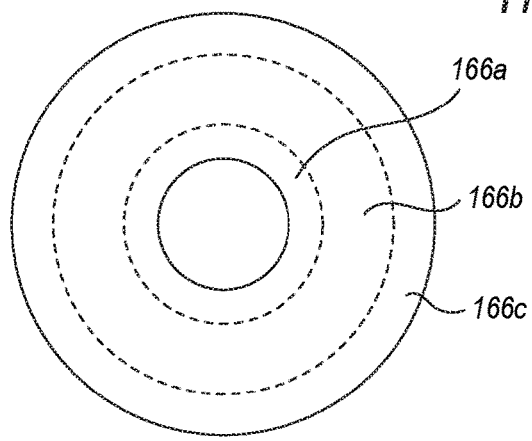
FIG. 6 illustrates a cross-sectional view of the universal connector shown in FIGS. 5A and 5B, the viewing plane passing through a fin of the connector.

FIG. 6 illustrates a cross-sectional view of a fin 154 having multiple flexion zones 166a-c indicated between dotted lines for clarification. The dotted lines represent flexion zone boundaries. In the illustrated embodiment, the fin 154 includes three flexion zones 166a-c configured radially around the fin 154. In one or more other embodiments, a fin 154 may have one, two, or more than three flexion zones 166. In addition, each flexion zone 166 of a fin 154 may have a radial dimension that is larger or smaller than others, or they may all have the same or similar radial dimensions. For instance, a first flexion zone may extend radially a certain distance, the second flexion zone may extend radially from the first flexion zone a certain distance, and the third flexion zone may extend radially from the second flexion zone a certain distance. The radial distance that each flexion zone extends may be equal to one another or may be different from one another.

In one embodiment, such as the embodiment illustrated in FIG. 6, each flexion zone 166a-c may have a different stiffness than an adjacent flexion zone 166a-c. For example, the innermost flexion zone 166a may be more or less stiff than the middle flexion zone 166b and the outermost flexion zone 166c may be more or less stiff than the middle flexion zone 166b and/or the innermost flexion zone 166a. In one embodiment, the flexion zones 166a-c may increase in stiffness from the outer edge radially inward towards the center of the fin 154. In another embodiment, the flexion zones 166a-c may decrease in stiffness from the outer edge radially inward towards the center of the fin 154. In yet another embodiment, the flexion zones 166a-c may alternate stiffness across the face of the fin 154 to form a bullseye pattern of stiffness on the fin 154.

Again, while FIG. 6 illustrates a fin 154 with three flexion zones 166a-c, one will appreciate that the number of flexion zones 166 may be more or less than three in one or more other embodiments. In addition, one or more other embodiments may include flexion zones 166 that extend radially outward from the center of the fin 154 to the outer edge of the fin 154, where multiple such flexion zones are disposed side by side around the circumference of the fin 154. In this way, the stiffness of the fin 154 may vary around the circumference thereof.

The dotted lines of FIG. 6, which indicate boundaries between various flexion zones 166a-c, are presented for illustrative purposes and are not meant to only indicate discrete transitions of stiffness between adjacent flexion zones 166. While one embodiment of the fin 154 may comprise discrete flexion zones 166 having abrupt transitions in stiffness therebetween, one or more other embodiments may include multiple flexion zones 166 that have gradual transitions in stiffness therebetween, or a combination of abrupt and gradual transitions. Again, the various flexion zones 166 may result from the various features described herein and/or a combination thereof, namely tapers 164, material thickness, fin extensions 162, and material properties of the fins 154 and fin extensions 162.

For example, in one embodiment, such as that shown in FIG. 5B, an abrupt change in stiffness at the outer edge of the fin 154 may occur where the taper 164 begins on the proximal face thereof. As another example, a gradual, continuous stiffness change may occur along the fin 154 where a taper 164 extends all the way down the fin 154 such that the fin 154 is thicker near the center and thinner towards the outer edge thereof. One will appreciate from the foregoing description that any number of stiffness profiles and flexion zone configurations are attainable by altering the geometry, thickness, materials, and other features of the fins 154.

The various combinations of flexion zones 166 described herein may affect how the universal connector 130 is retained within the receptacle 132 shown in FIG. 3. That is, the varying stiffness of each flexion zone 166 may cause each fin 154 to deform to a different degree within that zone, thus forming a deformation profile of the fin 154 when inserted into the receptacle 132 that is unique to each flexion zone configuration. Thus, by altering the configuration of the flexion zones 166 on the fins 154, one can achieve fin deformation profiles that best conform to a variety of receptacle features, such as receptacle threads, receptacle taper angles, and receptacle sizes.

Figure 7A:
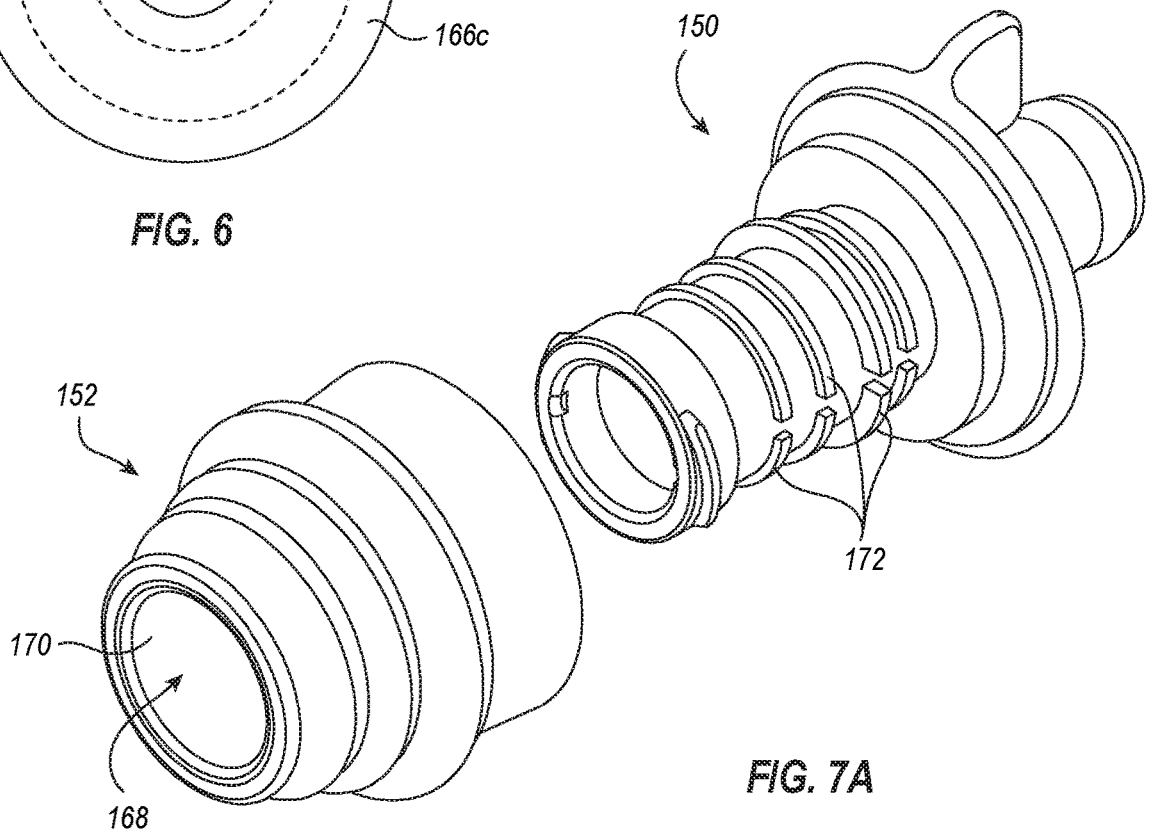
FIG. 7A illustrates a perspective exploded view of an exemplary universal fluid system connector, including a seal and a body of the connector.

Moving on to FIG. 7A, an exploded view is shown of the universal connector 130 with the seal 152 and the body 150. The seal 152 includes a passageway 168 through which the body 150 passes so that the seal 152 is disposed at least partially about the body 150. In one embodiment, the body 150 may be formed separately from the seal 152 and comprise material that is more rigid than the seal 152. For example, the body 150 may comprise ABS plastic material or any other suitably rigid polymer or other material such as, but not limited to, metals, composites, glasses, ceramics, and the like.

The seal 152 may comprise a flexible polymeric elastomer material having a Durometer Hardness, Shore A, of between about 35-80 points. In one embodiment, the seal 152 may comprise a flexible polymeric elastomer material having a Durometer Hardness, Shore A, of between about 45-65 points. In one embodiment, the seal 152 may comprise a flexible polymeric elastomer material having a Durometer Hardness, Shore A, of between about 50-60 points and preferably about 55 points.

Also, various portions of the seal 152, including the plurality of fins 154 and other portions of the seal 152 from which the fins 154 extend, may comprise materials having different Durometer Hardnesses. For example, in one embodiment, the seal 152 may comprise fins 154 that each have a different Durometer Hardness, either inside or outside of the Shore A point ranges noted above. In another embodiment, one or more of the plurality of fins 154 may have substantially the same Durometer Hardness while one or more other fins 154 of the same seal 152 may have a different Durometer Hardness. Furthermore, one or more of the plurality of fins 154 may have flexion zones with different Durometer Hardnesses. In yet another embodiment, the Durometer Hardness of one or more of the fins 154 may be greater or less than the Durometer Hardness of the portion of the seal 152 from which the fins 154 extend. Thus, in some embodiments, the various portions of the seal 152 may comprise different materials that result in any number of Durometer Hardness values and combinations thereof, either within and/or outside the Shore A point ranges noted above.

FIG. 7A also illustrates a body 150 having a plurality of ribs 172 projecting radially outward from the body 150 and at least partially surrounding the circumference of the body 150. In the embodiment illustrated in FIG. 7A, the ribs 172 have varying heights extending away from the body 150. The ribs 172 are also shown to have generally rectangular cross-sectional profiles. One or more other embodiments may comprise more or less ribs 150 than those shown on the body 150 in FIG. 7A. One or more other embodiments may also include ribs 172 having other cross-sectional profiles, such as triangular, circular, or the like. One or more other embodiments may include ribs 172 that extend all the way around the circumference of the body 150 and/or ribs 172 of varying heights and spaces between ribs 172.

Figure 7B:
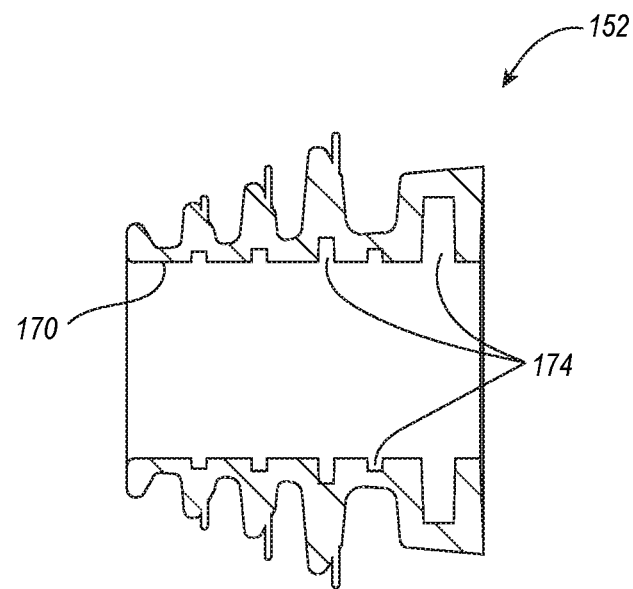
FIG. 7B illustrates a cross-sectional view of an exemplary seal of the universal fluid system connector.
Figure 7C:
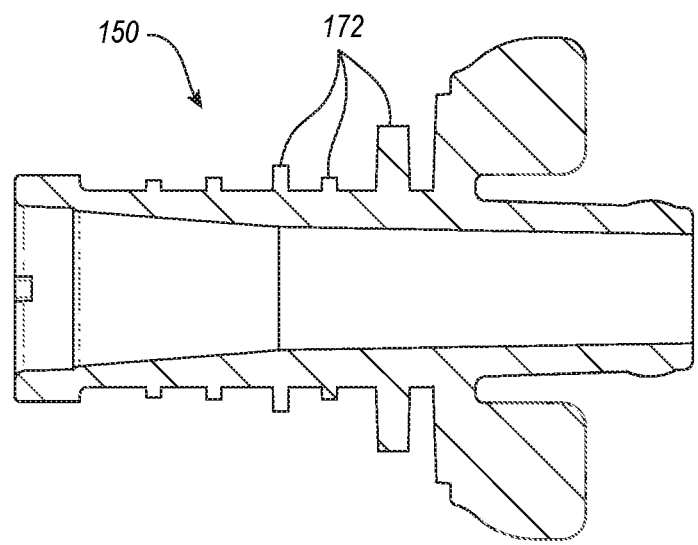
FIG. 7C illustrates a cross-sectional view of an exemplary body of the universal fluid system connector.

FIGS. 7B and 7C illustrate cross-sectional views of the seal 152 and body 150 illustrated in FIG. 7A. As illustrated in FIG. 7B, the seal 152 may comprise a plurality of recessed portions 174 extending into the internal surface 170 of the seal 152 that extend at least partially around the circumference of the internal surface 170 of the seal 152. The recessed portions 174 may correspond in position with the ribs 172 of the body 150 shown in FIG. 7C so that positioning the seal 152 at least partially about the body 150 results in the plurality of ribs 172 extending into the recessed portions 172 of the seal 152. Thus, in one embodiment, the cross-sectional shape of the recessed portions 174, as shown in the cross-sectional view of FIG. 7B, may correspond to the cross-sectional shape of the ribs 172 so that the ribs 172 retain the seal 152 at least partially about the body 150 during use.

Figure 7D:
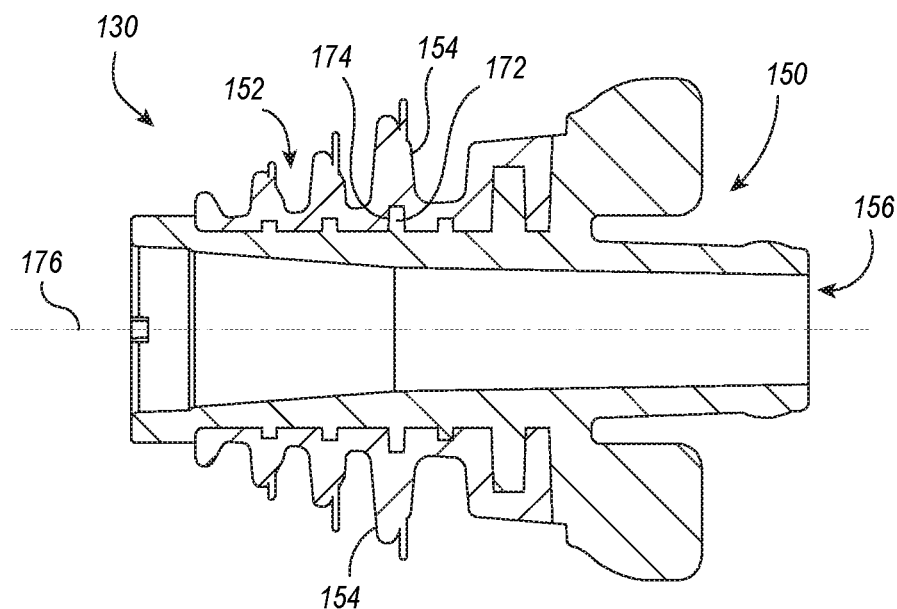
FIG. 7D illustrates a cross-sectional view of an exemplary universal fluid system connector.

Along these lines, FIG. 7D illustrates a cross-sectional view of the body 150 having the seal 152 retained together with the ribs 172 extending into and mating with the recessed portions 174. In one embodiment, one or more of the ribs 172 and recessed portions 174 may correspond in position to the fins 154, and one or more may not, as shown in FIG. 7D. In one embodiment, the seal 152 and body 150 may be separately manufactured and assembled together as described above. In one embodiment, the seal 152 and body 150 may be integrally formed, such as by molding or other manufacturing processes. In one embodiment, the fins 154 may be formed with the seal 152 as a single piece, either comprising the same or different material than the rest of the seal 152. In yet another embodiment, the fins 154 may be formed separately of the same or different material as the rest of the seal 152 and secured to the seal during manufacturing.

The height of each rib 172 and corresponding recessed portion 174 may also affect the flexibility of the fin 154 into which the rib 172 may extend. For example, as noted above, the body 150 and ribs 172 may comprise material that is more rigid than the seal 152 and fins 154. Thus, the further into the fin 154 a rib 172 extends, the greater the stiffness of the fin 154 in that area. Accordingly, the ribs 172 may produce or alter a flexion zone 166 of the fin 154, as described above. Likewise, a tapered rib 172 may cause a gradual change in flexion of the fin 154 into which the rib 172 extends as the rib 154 tapers thinner as the rib 172 extends radially outward.

Figure 8:
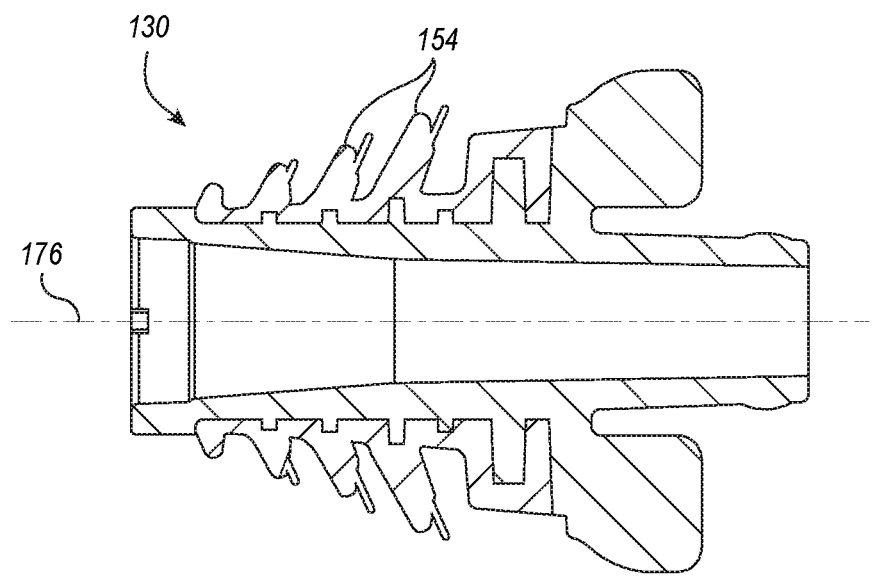
FIG. 8 illustrates a cross-sectional view of an exemplary universal fluid system connector having angled fins.
Figure 9:
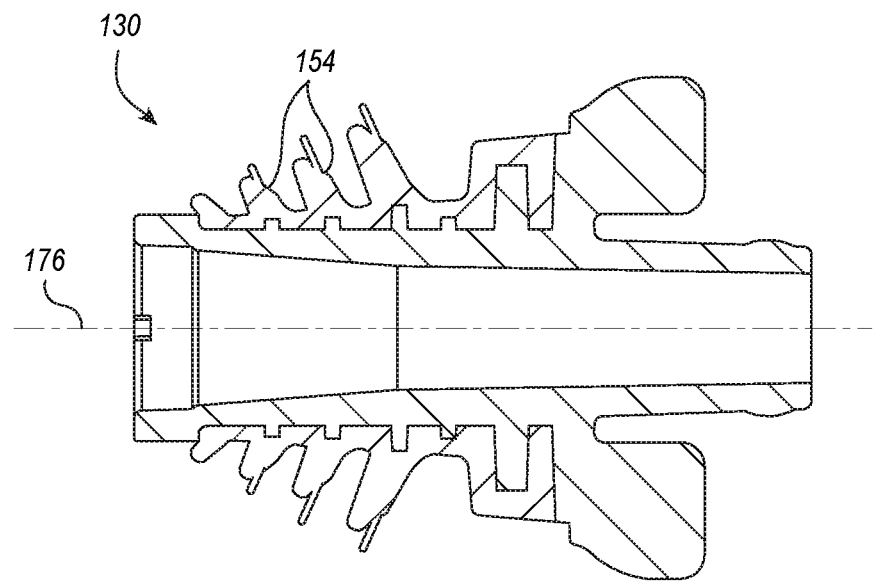
FIG. 9 illustrates a cross-sectional view of an exemplary universal fluid system connector having angled fins.

The various embodiments of universal connectors 130 described above include seals 152 having fins 154 that extend in a plane generally perpendicular to a central longitudinal axis 176 of the fluid passageway 156 of the body 150. However, one or more other embodiments may include fins 154 that extend radially outwardly from the body 150 at a non-perpendicular angle relative to the central longitudinal axis 176. For example, FIG. 8 illustrates a cross-sectional view of an embodiment of a universal connector 130 where the fins 154 extend proximally backwards at a non-perpendicular angle relative to the central longitudinal axis 176. Also, for example, FIG. 9 illustrates a cross-sectional view of an embodiment of a universal connector 130 having fins 154 extending distally forward at a non-perpendicular angle relative to the central longitudinal axis 176.

In one embodiment, the ribs 172 may be angled to correspond with the angled fins 154. In one embodiment, the fins 154 and/or ribs 172 may be angled to a greater degree or lesser degree than that shown in the figures. In one embodiment, the fins 154 of a single seal 152 may each be angled different than one another, either extending distally, perpendicularly, proximally, or a combination thereof. The angle of the fins 154 may affect the forces required to insert and remove the universal connector 130 into and from a receptacle 132.

For example, the embodiment shown in FIG. 8, having fins 154 extending proximally backwards, may require less force to insert into a receptacle and form an airtight connection than the force required to remove the universal connector 130 from the receptacle 312. This is because the fins 154 of this embodiment may need to deform to a greater degree back over the angle of the fins 154, as shown in FIG. 3, against the tapered wall 138 of the receptacle 138 when removed. Conversely, the embodiment shown in FIG. 9, having fins 154 extending distally forward, may require greater force to insert into a receptacle and form an airtight connection than the force required to remove the universal connector 130 from the receptacle 132.

Figure 10:
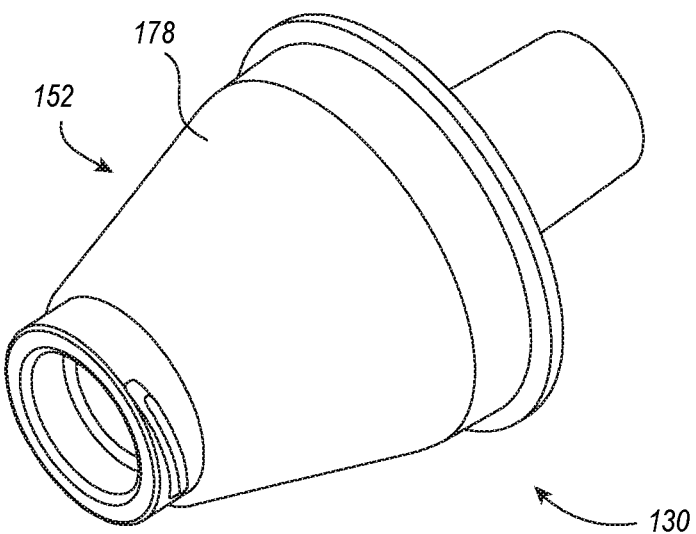
FIG. 10 illustrates a front perspective view of an exemplary universal fluid system connector.
Figure 11:
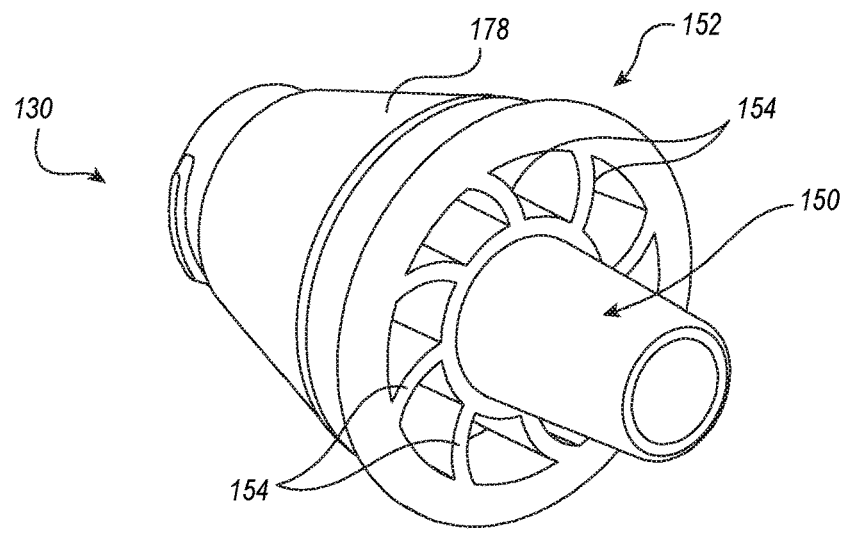
FIG. 11 illustrates a rear perspective view of the universal fluid system connector illustrated in FIG. 10.
Figure 12A:
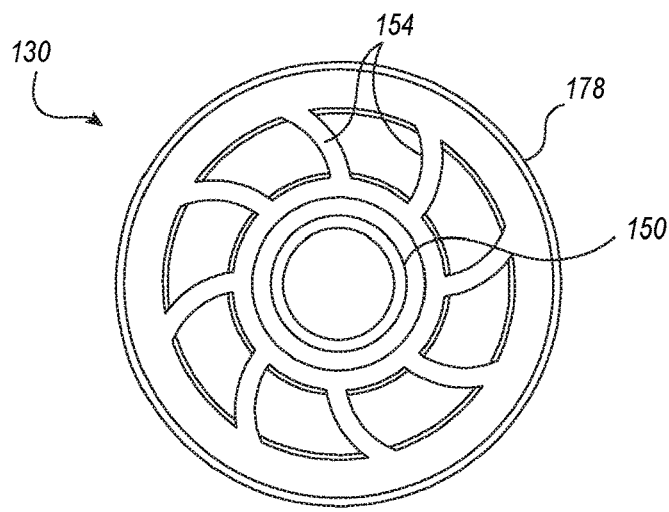
FIG. 12A illustrates a rear view of the universal fluid system connector illustrated in FIG. 10.
Figure 12B:
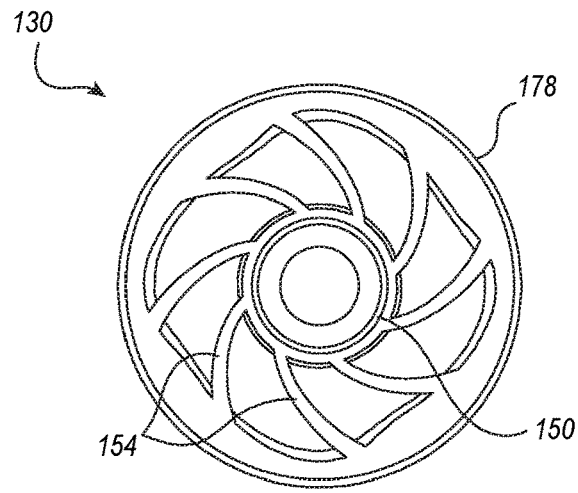
FIG. 12B illustrates a rear view of the fluid system connector illustrated in FIG. 10 in a partially compressed state.

Moving on to FIG. 10, a perspective view of another embodiment of a universal connector 130 is shown. In this embodiment, an outer frustoconical shell 178 at least partially surrounds the outer edges of the fins to form an outer surface of the seal 152. FIG. 11 shows a rear perspective view of the embodiment illustrated in FIG. 10. The fins 154 are each disposed along the length of the body 150 and curved so that the plurality of fins 154 spirals radially around at least a portion of the circumference of the body 150. The materials of the seal 152 and body 150 may be similar to the materials described for the seals 152 and bodies 150 described above with respect to other embodiments. Thus, the frustoconical shell 178 and fins 154 of the embodiment illustrated in FIGS. 10-12B may comprise flexible polymeric elastomer materials, while the body 150 may comprise more rigid materials, such as ABS plastic and the like.

Accordingly, when the universal connector 130 illustrated in FIGS. 10-12B is inserted into a receptacle 132, the frustoconical shell 178 may contract and the fins 154 may collapse radially inward towards the body 150 of the universal connector 130. The elastic fins 154 create a force opposing the tapered wall 138 of the receptacle 132 to hold the outer surface of the frustoconical shell 178 in the receptacle 132 via friction between the frustoconical shell 178 and the tapered wall 138 of the receptacle.

To better understand the embodiment illustrated in FIGS. 10 and 11, FIGS. 12A and 12B illustrate a rear view of the universal connector 130 shown in FIGS. 10 and 11. The universal connector 130 of FIG. 12A has not been inserted into a receptacle, so that the frustoconical shell 178 is not contracted and the curved fins 154 are fully extended. As described above, and as shown now in FIG. 12B, when the tapered wall of a receptacle exerts a force radially inwardly on the exterior of the frustoconical shell 178, the flexible frustoconical shell 178 contracts and the curved fins 154 collapse towards the body 150. The fins 154 are thus curved at a greater angle towards the body and the elasticity of the fins 154 exerts an outward force on the tapered wall of the receptacle so that the universal connector 130 is held within the receptacle via friction.

The frustoconical shell 178 and plurality of fins 154 extending longitudinally along the length of the body 150 may deform to different degrees along the length of the body 150. For example, if the tapered angle of the frustoconical shell 178 does not match the tapered angle of the tapered wall of the receptacle, the distal end of the frustoconical shell 178 may contract more than the proximal end, or vice versa, to accommodate the taper angle of the receptacle. The frustoconical shell 178 may also deform around other receptacle features, such as threads, to form an airtight seal. In this way, the embodiment of the universal connector illustrated in FIGS. 10-12B may form an airtight seal within a wide range of receptacles.

Attention is now directed to FIGS. 13-16, which illustrate another example embodiment of a universal connector 180 according to the present disclosure. Universal connector 180 may be similar or identical in many respects to the universal connectors 130 disclosed herein. For instance, other than the proximal stem and swivel discussed below, the universal connector 180 may be substantially identical to the universal connector 130 shown in FIGS. 3-5B. By way of example, the body, seal, and tabs of universal connector 180 may be the same or substantially the same as those shown in FIGS. 3-5B. Similarly, the universal connector 130 shown in FIGS. 10-12B may be modified to include a stem and swivel as discussed below.

Figure 13:
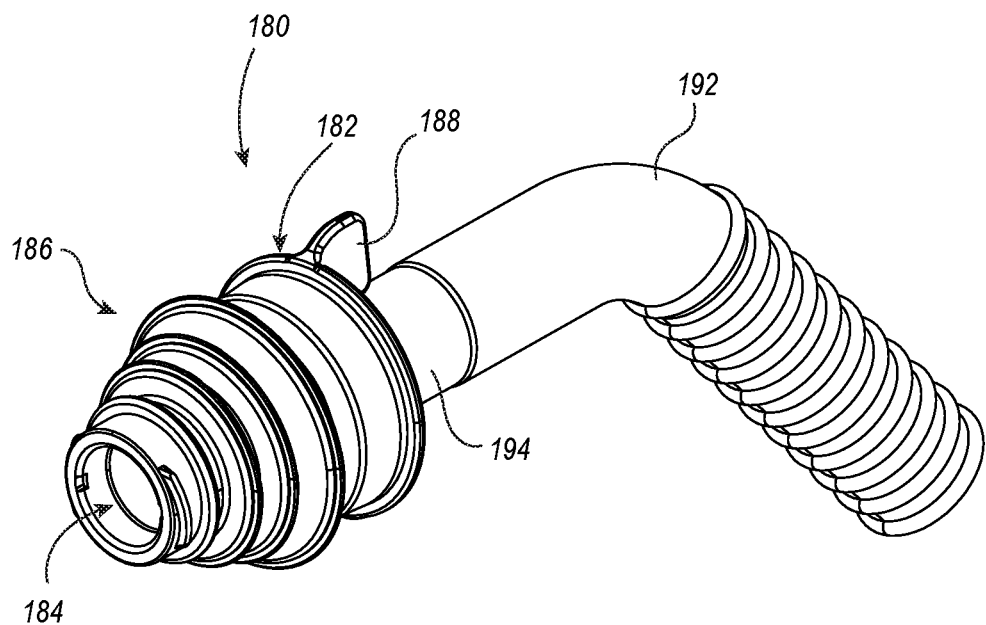
FIG. 13 illustrates a perspective view of another exemplary universal fluid system connector.
Figure 14:
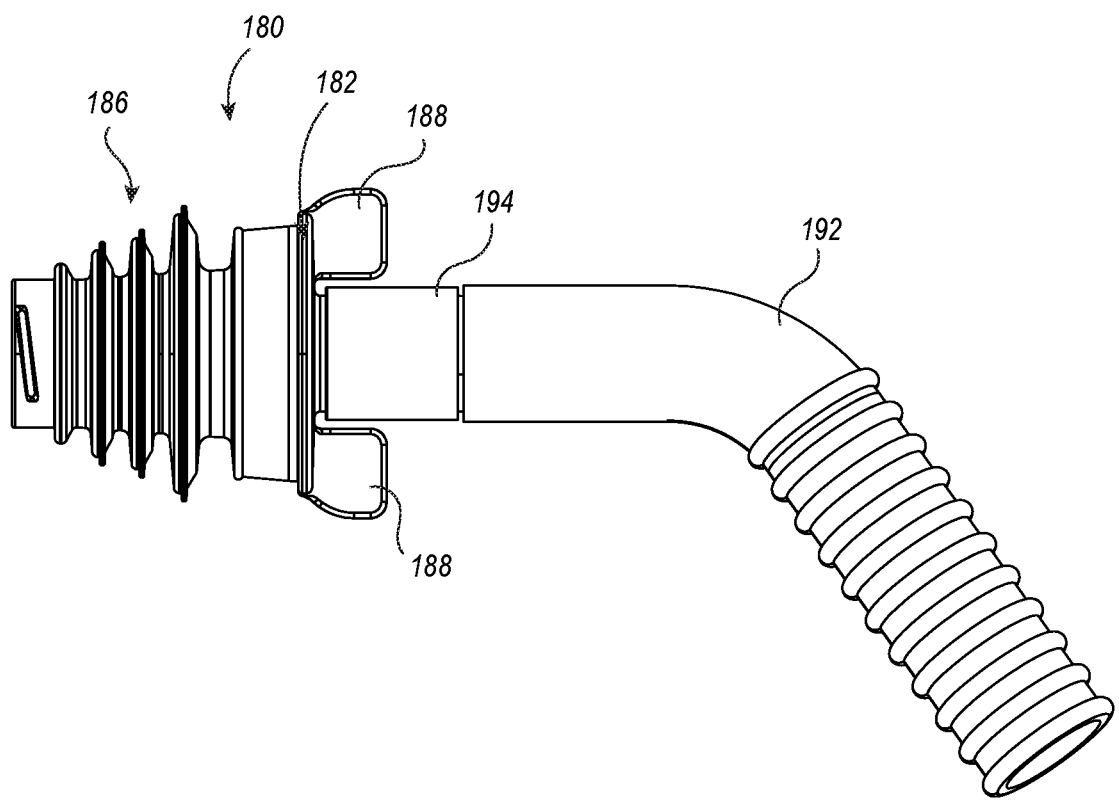
FIG. 14 illustrates a side view of the exemplary universal fluid system connector of FIG. 13.
Figure 15:
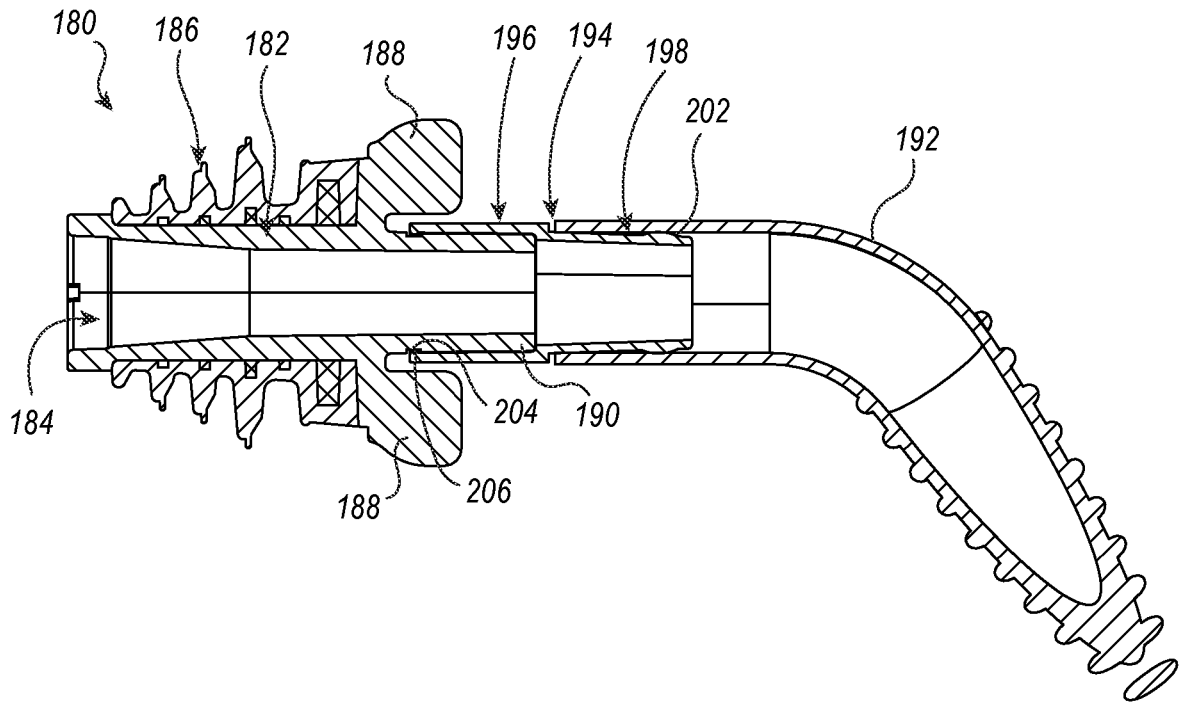
FIG. 15 illustrates side cross-sectional view of the exemplary universal fluid system connector of FIG. 13.

In FIGS. 13-15, the universal connector 180 generally includes a body 182 with a fluid passageway 184 extending therethrough. A seal 186 is disposed on a portion of the body 182. Tabs 188 extend proximally from the body 182. As can be seen in FIG. 15, the universal connector 180 also includes a proximally extending stem 190.

The universal connector 180 is also connected to a vacuum hose 192. Unlike the previously described universal connectors, the vacuum hose 192 is not mounted directly on the stem of the universal connector 180. Rather, the universal connector 180 and the hose 192 are connected together via a swivel 194. Connecting the universal connector 180 and the hose 192 together with swivel 194 enables relative rotation between the universal connector 180 and the hose 192.

Figure 16:
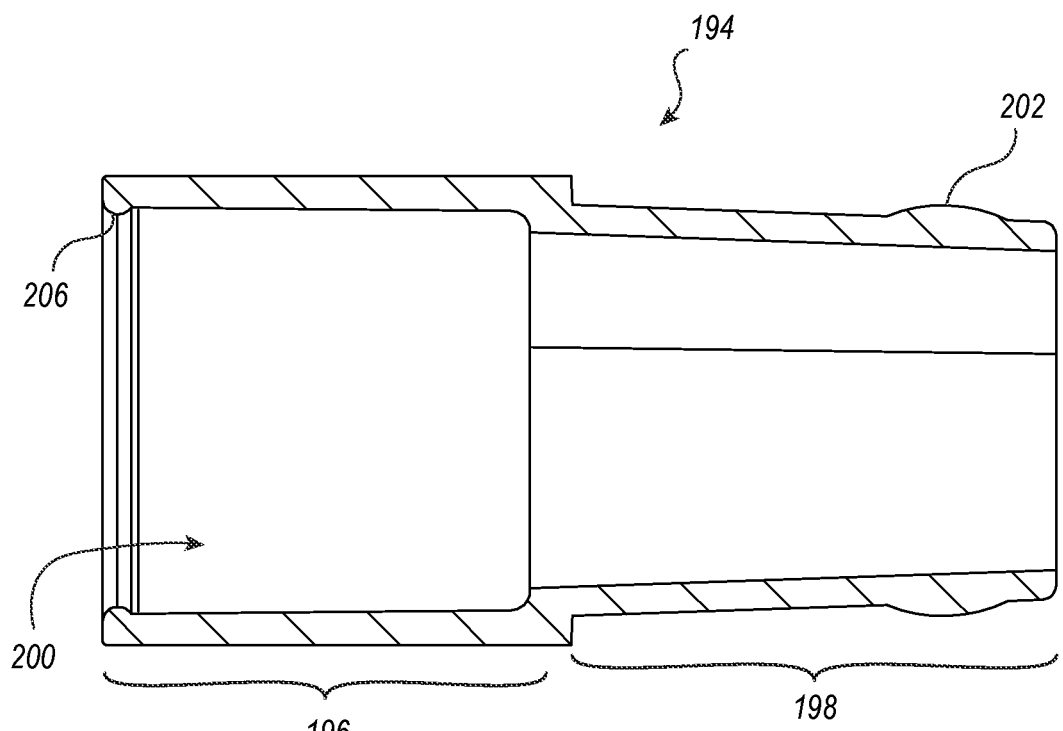
FIG. 16 illustrates a cross-sectional view of a swivel for use with a universal connector.

FIG. 15 illustrates the universal connector 180, the hose 192, and the swivel 194 in cross-section to show how the components are associated with one another. FIG. 16 illustrates just the swivel 194 in cross-section. In the illustrated embodiment, the swivel 194 includes a female portion 196 and a male portion 198. A fluid passageway 200 extends through the swivel 194. The female portion 196 includes an open distal end that is sized and shaped to receive therein at least a portion of the stem 190 of the universal connector 180. The male portion 198 can be substantially similar or identical to the stem 157 described above in connection with FIGS. 3-5B. For instance, the male portion 198 may have a tapered outer surface and a hose retaining lip 202 disposed thereon.

As can be seen in FIG. 15, the male portion 198 can be inserted into an open end of the hose 192. The interface between the hose retaining lip 202 and the interior of the hose 192 can form a seal therebetween and secure the hose 192 to the swivel 194. Similarly, the stem 190 of the universal connector 180 can be inserted into the open end of the female portion 196 of the swivel 194. The exterior surface of the stem 190 and the interior surface of the female portion 196 may interact to create a seal therebetween. Alternatively, one or more seals may be disposed between the stem 190 and the swivel 194 to seal the connection therebetween.

As can also be seen in FIGS. 15 and 16, the stem 190 and the swivel 194 may include cooperating features that can secure the swivel 194 to the universal connector 180 and enable relative rotation therebetween. In the illustrated embodiment, for example, the stem 190 includes an annular groove 204 disposed around at least a portion of the outer surface thereof. The female portion 196 includes a complementary rim 206 formed on an interior surface thereof. When assembled as shown in FIG. 15, the rim 206 extends into the annular groove 204. The interaction between the rim 206 and groove 204 can secure the swivel 194 to the universal connector 180. Additionally, the interaction between the rim 206 and the groove 204 can enable relative rotation between the swivel 194 (and associated hose 192) and the universal connector 180.

While the swivel 194 is shown and described as having a female portion that receives part of the universal connector 180 therein, it will be appreciated that the arrangement could be reversed. For instance, the stem 190 could be sized to receive a portion of the swivel therein. The portion of the swivel received inside of the stem would then be considered a male portion. Likewise, the male portion 198 could be configured as a female portion that could receive the end of the hose 192 therein. Thus, generally speaking, the swivel could include a first mating portion and a second mating portion. In some embodiments, the first and second mating portions could be male and female portions, both could be male portions, or both could be female portions. Likewise, the universal connector may have either a male or female mating portion depending on whether the swivel has a male or female mating portion. Similarly, the vacuum hose may have either a male or female mating portion depending on whether the swivel has a male or female mating portion.

It will also be appreciated that other arrangements described above could be reversed. For instance, the stem 190 may include a radially extending rim and the interior surface of the female portion 196 may include an annular groove that receives the rim therein. Similarly, if the hose 192 is received within a portion of the swivel (as opposed to over the swivel as illustrated), the interior of the swivel could include the hose retaining lip 202.

It will further be appreciated that the shown and described swivel and associated connections with the universal connector 180 and hose 192 are merely exemplary. Other swivels and associated connection features may be included and are contemplated within the scope of this disclosure. Thus, for example, any swivel may be used to connect the universal connector and the hose together such relative rotation between the universal connector and the hose is enabled. As described above, the swivel may be able to rotate relative to one of the universal connector and the hose. In other embodiments, the swivel may be able to rotate relative to both the universal connector and the hose. In still other embodiments, the swivel may include a first half and a second half that are able to rotate relative to one another. The first half may be connected to the universal connection in a fixed or swiveling fashion. Likewise, the second half may be connected to the hose in a fixed or swiveling fashion. In any event, the first and second halves may swivel relative to one another, thereby enabling relative rotation between the universal connector and the hose.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A universal fluid system connector assembly, comprising:
   a body having a length extending between a distal end thereof and a proximal end thereof;
   a seal disposed about at least a portion of the body between the proximal and distal ends of the body, the seal having an inner surface disposed adjacent to the body and a plurality of flexible fins disposed along the length of the body, each fin having a diameter and extending radially out away from the inner surface and the body;
   a stem connected to or integrally formed with the body, at least a portion of the stem extending proximally from the proximal end of the body and a proximal end of the seal; and
   a swivel connectable to the stem, at least a portion of the seal not being covered by the swivel when the swivel is connected to the stem, the swivel being configured to connect to a vacuum hose and enable relative rotation between the body and the hose, the swivel comprising a first mating portion and a second mating portion, the second mating portion comprising a male portion configured to be inserted at least partially within an end of a vacuum hose.

2. The universal fluid system connector assembly of claim 1, wherein the seal further comprises an outer frustoconical shell disposed at least partially around the plurality of fins.

3. The universal fluid system connector assembly of claim 1, wherein the first mating portion comprises a female portion sized and configured to receive therein at least a portion of the stem of the body.

4. The universal fluid system connector assembly of claim 3, wherein the stem comprises an annular groove disposed in an outer surface thereof and the female portion of the swivel comprises a rim on an interior surface thereof, the annular groove and the rim being configured to rotationally connect the swivel to the body.

5. The universal fluid system connector assembly of claim 1, wherein the plurality of flexible fins extend circumferentially at least partially about the body.

6. The universal fluid system connector assembly of claim 1, wherein the male portion comprises a hose retaining lip disposed on an outer surface thereof.

7. The universal fluid system connector assembly of claim 1, wherein the male portion comprises an outer dimension that decreases in the proximal direction.

8. The universal fluid system connector assembly of claim 1, wherein the swivel comprises a fluid passageway extending therethrough.

9. The universal fluid system connector assembly of claim 1, wherein the plurality of fins comprises three fins and wherein a difference between the diameters of the most distal fin and the second most distal fin is less than a difference between the diameters of the most proximal fin and the second most proximal fin.

10. The universal fluid system connector assembly of claim 1, wherein each fin comprises a taper.

11. The universal fluid system connector assembly of claim 1, wherein each fin comprises a first flexion zone and second flexion zone, the first flexion zone comprising a first outer ring portion of the fin including an outer edge of the fin and the second flexion zone comprising an inner ring portion of the fin disposed radially inward from the first flexion zone.

12. A fluid system connector assembly, comprising:
a body comprising:
a length extending between a distal end thereof and a proximal end thereof;
a fluid passageway extending through the length of the body;
a proximally extending stem; and
a plurality of ribs disposed along at least a portion of the length of the body, each rib extending at least partially around the body and extending radially outward from the body; and
a seal disposed about at least a portion of the body, the seal comprising:
a plurality of flexible fins disposed along the length of the body, outer edges of the plurality of fins forming a frustoconical shape tapering downward toward the distal end; and
a plurality of recessed portions extending radially outwardly from an interior surface of the seal, each recessed portion disposed at least partially around a circumference of the interior surface of the seal, wherein the plurality of ribs corresponds in position with the plurality of recessed portions so that the ribs mate with the recessed portions to retain the seal about the body; and
a swivel connectable to the stem, the swivel being configured to facilitate relative rotational movement between the body and a vacuum hose connected to the swivel.

13. The fluid system connector assembly of claim 12, wherein the seal comprises a flexible polymeric elastomer having a Durometer Hardness, Shore A, of between about 35-80 points, about 45-65 points, or about 50-60 points.

14. The fluid system connector assembly of claim 12, wherein the body further comprises one or more tabs extending proximally therefrom, the tabs being configured to aid in a manipulation of the fluid system connector.

15. The fluid system connector assembly of claim 12, wherein the swivel comprises a female portion configured to receive at least a portion of the stem therein, such that the swivel and the body can rotate relative to one another.

16. The fluid connector system of claim 12, wherein the swivel comprises a male portion configured to be inserted into an open end of a vacuum hose.

17. A fluid system connector assembly, comprising:
a body having a length extending between a distal end thereof and a proximal end thereof, the body comprising a proximally extending stem; and
a seal disposed about at least a portion of the body, the seal comprising:
a plurality of flexible fins disposed along the length of the body so that outer edges of the fins form a frustoconical shape along the length of the body that tapers down towards the distal end, wherein each fin is curved so that the plurality of fins spirals radially around at least a portion of the body; and
an outer frustoconical shell disposed at least partially around the plurality of fins and connected to the outer edges of the fins; and
a swivel connectable to the stem, the swivel being configured to facilitate relative rotational movement between the body and a vacuum hose connected to the swivel.

18. The fluid system connector assembly of claim 17, further comprising the vacuum hose connectable to the swivel.

19. The fluid system connector assembly of claim 18, wherein the swivel comprises:
a male portion configured to be inserted into an open end of the vacuum hose; and
a female portion configured to receive therein at least a portion of the stem.

20. The fluid system connector assembly of claim 19, wherein one or more of:
the male portion comprises a hose retaining lip configured to secure the hose on the male portion; or
the stem and the female portion comprise a complimentary annular groove and rim configured to rotationally connect the body and the swivel.

* * * * *